United States Patent
Lant et al.

(10) Patent No.: US 10,526,565 B2
(45) Date of Patent: *Jan. 7, 2020

(54) DETERGENT COMPOSITION

(71) Applicant: The Procter & Gamble Company, Cincinnati, OH (US)

(72) Inventors: Neil Joseph Lant, Newcastle upon Tyne (GB); Jean-Luc Philippe Bettiol, Etterbeek (BE); Denis Alfred Gonzales, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,204

(22) Filed: May 9, 2017

(65) Prior Publication Data
US 2017/0321162 A1 Nov. 9, 2017

(30) Foreign Application Priority Data

May 9, 2016 (EP) .................................... 16168822

(51) Int. Cl.
| | | |
|---|---|---|
| *C12N 9/88* | (2006.01) | |
| *C11D 3/386* | (2006.01) | |
| *C11D 1/94* | (2006.01) | |
| *C11D 3/04* | (2006.01) | |
| *C11D 3/33* | (2006.01) | |
| *C11D 3/36* | (2006.01) | |
| *C11D 11/00* | (2006.01) | |
| *C11D 1/75* | (2006.01) | |
| *C11D 1/90* | (2006.01) | |

(52) U.S. Cl.
CPC ............ *C11D 3/38636* (2013.01); *C11D 1/94* (2013.01); *C11D 3/04* (2013.01); *C11D 3/33* (2013.01); *C11D 3/361* (2013.01); *C11D 3/386* (2013.01); *C11D 3/38627* (2013.01); *C11D 3/38645* (2013.01); *C11D 11/0023* (2013.01); *C12Y 114/00* (2013.01); *C12Y 302/01* (2013.01); *C12Y 302/01004* (2013.01); *C12Y 304/00* (2013.01); *C11D 1/75* (2013.01); *C11D 1/90* (2013.01)

(58) Field of Classification Search
CPC ................. C12N 9/88; C11D 3/38636; C12Y 402/01053
USPC .................................................. 435/232, 177
See application file for complete search history.

(56) References Cited

U.S. PATENT DOCUMENTS

| | | |
|---|---|---|
| 5,705,465 A | 1/1998 | Angevaare |
| 5,851,973 A | 12/1998 | Foley |
| 6,372,708 B1 | 4/2002 | Kasturi |
| 6,492,316 B1 | 12/2002 | Herbots |
| 6,699,828 B1 | 3/2004 | De Buzzaccarini |
| 8,137,477 B2 | 3/2012 | Wittorff |
| 8,293,697 B2* | 10/2012 | Boutique ................. C11D 1/02 510/300 |
| 8,940,677 B2 | 1/2015 | Boutique |
| 2003/0191043 A1 | 10/2003 | Becker |
| 2009/0142821 A1* | 6/2009 | Cirino .................. C12N 9/0071 435/189 |
| 2009/0203568 A1* | 8/2009 | Souter ................ C11D 3/38627 510/321 |
| 2012/0157717 A1* | 6/2012 | Rude .................... C12N 9/0006 568/28 |
| 2012/0227120 A1 | 9/2012 | Hitchman |
| 2013/0175196 A1 | 7/2013 | Dale |
| 2014/0322770 A1 | 10/2014 | Landvik |
| 2015/0184208 A1 | 7/2015 | Oestergaard |
| 2017/0321160 A1 | 11/2017 | Lant |
| 2017/0321161 A1 | 11/2017 | Lant |

FOREIGN PATENT DOCUMENTS

EP          0399681 A3      1/1991

OTHER PUBLICATIONS

Rude et al. Applied Environmental Microbiology 77(5): 1718-1727 (2011).*
Belcher, James, et al.—Structure and Biochemical Properties of the Alkene Producing Cytochrome P450 OleT JE (CYP152L1) from the *Jeotgalicoccus* sp. 8456 Bacterium*—The Journal of Biological Chemistry, vol. 289, No. 10, pp. 6535-6550, Mar. 7, 2014.
Bevers, Loes E., et al.—Oleate Hydratase Catalyzes the Hydration of a Nonactivated Carbon-Carbon Bond—Journal of Bacteriology, Aug. 1, 2009, pp. 5010-5012, vol. 191, No. 15.
Davis, S. Christopher, et al.—Oxidation of w-Oxo Fatty Acids by Cytochrome P450 BM-3 (CYP102)—Archives of Biochemistry and Biophysics, vol. 328, No. 1, Apr. 1, 1996, pp. 35-42.
Engleder, Matthias, et al.—Structure-Based Mechanism of Oleate Hydratase from Elizabethkingia Meningoseptica—Chembiochem—A European Journal of Chemical Biology, Aug. 17, 2015, pp. 1730-1734, vol. 16, No. 12.
Girvan, Hazel M., et al.—Applications of Microbial Cytochrome P450 Enzymes in Biotechnology and Synthetic Biology—Current Opinion in Chemical Biology 2016, 31:136-145, www.sciencedirect.com.
International Search Report for International Application Serial No. PCT/US2017/031665, dated Jul. 18, 2017, 15 pages.
Yesiloglu, Yesim, et al.—Lipase-Catalized Esterification of Glycerol and Oleic Acid—Journal of the American Oil Chemists Society, Mar. 1, 2004, pp. 281-284, vol. 81, No. 3.

* cited by examiner

*Primary Examiner* — Tekchand Saidha
(74) *Attorney, Agent, or Firm* — Melissa G. Krasovec

(57) ABSTRACT

A detergent composition, preferably a manual dishwashing detergent composition comprising a surfactant system and a fatty acid decarboxylase enzyme and method of manually washing soiled articles, comprising the step of: delivering a composition to a volume of water to form a wash liquor and immersing the soiled articles, in the wash liquor, or delivering a composition optionally in the presence of water, directly onto a soiled article, or onto a cleaning implement, and using the cleaning implement to clean the soiled article.

19 Claims, No Drawings

Specification includes a Sequence Listing.

SEQUENCE LISTING

<160> NUMBER OF SEQ ID NOS: 2

<210> SEQ ID NO 1
<211> LENGTH: 422
<212> TYPE: PRT
<213> ORGANISM: Jeotgalicoccus sp. 8456

<400> SEQUENCE: 1

```
Met Ala Thr Leu Lys Arg Asp Lys Gly Leu Asp Asn Thr Leu Lys Val
1               5                   10                  15

Leu Lys Gln Gly Tyr Leu Tyr Thr Thr Asn Gln Arg Asn Arg Leu Asn
                20                  25                  30

Thr Ser Val Phe Gln Thr Lys Ala Leu Gly Gly Lys Pro Phe Val Val
            35                  40                  45

Val Thr Gly Lys Glu Gly Ala Glu Met Phe Tyr Asn Asn Asp Val Val
50                  55                  60

Gln Arg Glu Gly Met Leu Pro Lys Arg Ile Val Asn Thr Leu Phe Gly
65                  70                  75                  80

Lys Gly Ala Ile His Thr Val Asp Gly Lys Lys His Val Asp Arg Lys
                85                  90                  95

Ala Leu Phe Met Ser Leu Met Thr Glu Gly Asn Leu Asn Tyr Val Arg
            100                 105                 110

Glu Leu Thr Arg Thr Leu Trp His Ala Asn Thr Gln Arg Met Glu Ser
        115                 120                 125

Met Asp Glu Val Asn Ile Tyr Arg Glu Ser Ile Val Leu Leu Thr Lys
130                 135                 140

Val Gly Thr Arg Trp Ala Gly Val Gln Ala Pro Pro Glu Asp Ile Glu
145                 150                 155                 160

Arg Ile Ala Thr Asp Met Asp Ile Met Ile Asp Ser Phe Arg Ala Leu
                165                 170                 175

Gly Gly Ala Phe Lys Gly Tyr Lys Ala Ser Lys Glu Ala Arg Arg Arg
            180                 185                 190

Val Glu Asp Trp Leu Glu Glu Gln Ile Ile Glu Thr Arg Lys Gly Asn
        195                 200                 205

Ile His Pro Pro Glu Gly Thr Ala Leu Tyr Glu Phe Ala His Trp Glu
    210                 215                 220

Asp Tyr Leu Gly Asn Pro Met Asp Ser Arg Thr Cys Ala Ile Asp Leu
225                 230                 235                 240

Met Asn Thr Phe Arg Pro Leu Ile Ala Ile Asn Arg Phe Val Ser Phe
                245                 250                 255

Gly Leu His Ala Met Asn Glu Asn Pro Ile Thr Arg Glu Lys Ile Lys
            260                 265                 270

Ser Glu Pro Asp Tyr Ala Tyr Lys Phe Ala Gln Glu Val Arg Arg Tyr
        275                 280                 285

Tyr Pro Phe Val Pro Phe Leu Pro Gly Lys Ala Lys Val Asp Ile Asp
    290                 295                 300

Phe Gln Gly Val Thr Ile Pro Ala Gly Val Gly Leu Ala Leu Asp Val
305                 310                 315                 320

Tyr Gly Thr Thr His Asp Glu Ser Leu Trp Asp Asp Pro Asn Glu Phe
                325                 330                 335
```

```
Arg Pro Glu Arg Phe Glu Thr Trp Asp Gly Ser Pro Phe Asp Leu Ile
            340                 345                 350

Pro Gln Gly Gly Gly Asp Tyr Trp Thr Asn His Arg Cys Ala Gly Glu
            355                 360                 365

Trp Ile Thr Val Ile Ile Met Glu Gly Thr Met Lys Tyr Phe Ala Glu
370                 375                 380

Lys Ile Thr Tyr Asp Val Pro Glu Gln Asp Leu Glu Val Asp Leu Asn
385                 390                 395                 400

Ser Ile Pro Gly Tyr Val Lys Ser Gly Phe Val Ile Lys Asn Val Arg
            405                 410                 415

Glu Val Val Asp Arg Thr
            420

<210> SEQ ID NO 2
<211> LENGTH: 261
<212> TYPE: PRT
<213> ORGANISM: Pseudomonas protegens

<400> SEQUENCE: 2

Met Ile Asp Thr Phe Ser Arg Thr Gly Pro Leu Met Glu Ala Ala Ser
1               5                   10                  15

Tyr Pro Ala Trp Thr Gln Gln Leu Ile Gln Asp Cys Ser Glu Ser Lys
            20                  25                  30

Arg Arg Val Val Glu His Glu Leu Tyr Gln Arg Met Arg Asp Asn Lys
        35                  40                  45

Leu Ser Ala Lys Val Met Arg Gln Tyr Leu Ile Gly Gly Trp Pro Val
    50                  55                  60

Val Glu Gln Phe Ala Leu Tyr Met Ala Gln Asn Leu Thr Lys Thr Arg
65                  70                  75                  80

Phe Ala Arg His Pro Gly Glu Asp Met Ala Arg Arg Trp Leu Met Arg
                85                  90                  95

Asn Ile Arg Val Glu Leu Asn His Ala Asp Tyr Trp Val His Trp Ser
            100                 105                 110

Arg Ala His Gly Val Thr Leu Glu Asp Leu Gln Ala Gln Gln Val Pro
        115                 120                 125

Pro Glu Leu His Ala Leu Ser His Trp Cys Trp His Thr Ser Ser Ala
    130                 135                 140

Asp Ser Leu Ile Val Ala Ile Ala Ala Thr Asn Tyr Ala Ile Glu Gly
145                 150                 155                 160

Ala Thr Gly Glu Trp Ser Ala Leu Val Cys Ser Asn Gly Ile Tyr Ala
                165                 170                 175

Ala Ala Phe Pro Glu Glu Asp Arg Lys Arg Ala Met Lys Trp Leu Lys
            180                 185                 190

Met His Ala Gln Tyr Asp Asp Ala His Pro Trp Glu Ala Leu Glu Ile
        195                 200                 205

Ile Val Thr Leu Ala Gly Leu Asn Pro Thr Lys Ala Leu Gln Ala Glu
    210                 215                 220

Leu Arg Gln Ala Ile Cys Lys Ser Tyr Asp Tyr Met Tyr Leu Phe Leu
225                 230                 235                 240

Glu Arg Cys Met Gln Gln Glu Lys Thr Ala Val Thr Arg Glu Arg Leu
                245                 250                 255

Ala Leu Ala Glu Gly
            260
```

DETERGENT COMPOSITION

REFERENCE TO A SEQUENCE LISTING

This application contains a Sequence Listing in computer readable form. The computer readable form is incorporated herein by reference.

FIELD OF THE INVENTION

The present invention relates to a detergent composition comprising a surfactant system and a fatty acid decarboxylase enzyme. Preferably the composition is for use in a laundry or dish washing process, and may be particularly useful for use in a manual washing process, i.e. for washing by hand or in a non-fully automated washing machine, such as semi-automatic washing machine (e.g. twin-tub etc.). Preferably the composition is a dishwashing detergent composition. Preferred compositions are in liquid form.

BACKGROUND OF THE INVENTION

Detergent compositions should have a good suds profile while providing good soil and grease cleaning. Users usually see foam as an indicator of the performance of the detergent composition. Moreover, the user of a detergent composition may also use the suds profile and the appearance of the foam (density, whiteness) as an indicator that the wash solution still contains active detergent ingredients. This is particularly the case for manual washing, also referred to herein as hand-washing, where the user usually doses the detergent composition depending on the suds remaining and renews the wash solution when the suds/foam subsides or when the foam does not look thick enough. Thus, a detergent composition, particularly a manual wash detergent composition that generates little or low density foam would tend to be replaced by the user more frequently than is necessary.

Thus, it is desirable for a detergent composition to provide good cleaning and also good foam height and density as well as good foam duration during the initial mixing of the detergent with water and during the entire washing operation. When used in a hand-washing process, the composition preferably also provides a pleasant washing experience, i.e, good feel on the user's hands during the wash. Preferably detergent compositions are also easy to rinse. Preferably in addition, the composition provides a good finish to the washed items.

It has been found that some types of soil, in particular greasy soils, act as a foam suppressor as they are removed from soiled articles into the wash liquor, triggering consumers to replace the product more frequently than is necessary. As such there is a need to provide detergent compositions with desirable foam and cleaning properties, especially over time as greasy soils are removed from soiled articles. Typical oily/greasy soils include cooking oils for example, plant oils such as palm kernel oil, coconut oil and olive oil, and animal soils such as animal fats and body soils such as sebum.

SUMMARY OF THE INVENTION

According to the present invention there is provided a detergent composition comprising a fatty acid decarboxylase enzyme and a surfactant system.

Preferably the detergent composition is a manual-washing composition. Preferably the detergent composition is for manual dishwashing. Preferably the detergent composition comprises a laundry washing composition, which may be particularly preferred for washing delicate fabrics. Compositions may be particulate or liquid or a combination thereof. Preferred compositions are in the form of a liquid, optionally enclosed in a water soluble film in the form of a pouch, preferably a multi-compartment pouch, optionally with a particulate composition in at least one compartment.

The invention also provides a method of washing soiled articles comprising forming a wash liquor comprising a surfactant system and a fatty acid decarboxylase enzyme, contacting the articles with the wash liquor, and optionally rinsing and drying.

The invention also provides a method of washing soiled articles comprising contacting a soiled article directly with the composition, optionally using a cleaning device, and then contacting the soiled article and detergent composition with water for further cleaning and/or rinsing.

The composition of the invention provides good cleaning and good suds profile, especially in the presence of greasy soils. The compositions of the present invention have been found to be particularly useful as fatty acids build up in the wash liquor. These may be present either in the soil or released to the wash liquor during removal of soils which break down to generate fatty acids.

According to the present invention, there is provided a method of manual washing comprising the step of: delivering the detergent composition to a volume of water and immersing soiled articles in the water. When the composition of the invention is used according to this method an excellent suds profile, with a long lasting effect is achieved.

According to the present invention, there is provided a method of manual washing comprising the step of: delivering the detergent composition of the invention directly onto soiled articles or onto a cleaning implement and using the cleaning implement to clean the soiled articles. Preferably the cleaning implement is a sponge and more preferably the sponge is wet.

Preferably the manual washing is dishwashing and the soiled articles comprise soiled dishware. As used herein, "dishware" includes cookware and tableware.

DETAILED DESCRIPTION OF THE INVENTION

Definitions

As used herein, the articles "a" and "an" when used in a claim, are understood to mean one or more of what is claimed or described.

As used herein, the term "substantially free of" or "substantially free from" means that the indicated material is present in an amount of no more than about 5 wt %, preferably no more than about 2%, and more preferably no more than about 1 wt % by weight of the composition.

As used therein, the term "essentially free of" or "essentially free from" means that the indicated material is present in an amount of no more than about 0.1 wt % by weight of the composition, or preferably not present at an analytically detectable level in such composition. It may include compositions in which the indicated material is present only as an impurity of one or more of the materials deliberately added to such compositions.

As used herein the phrase "cleaning composition," "detergent composition," or "detergent or cleaning composition" are used interchangeably herein to refer to compositions and formulations designed for cleaning soiled articles. Such compositions include but are not limited to, dish-washing compositions, laundry detergent compositions, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, dish washing compositions, hard surface cleaning compositions, unit dose formulation, delayed delivery formulation, detergent contained on or in a porous substrate or nonwoven sheet, and other suitable forms that may be apparent to one skilled in the art in view of the teachings herein. Such compositions may be used as a pre-cleaning treatment, a post-cleaning treatment, or may be added during the rinse or wash cycle of the cleaning process. The cleaning compositions may have a form selected from liquid, powder, single-phase or multi-phase unit dose or pouch form, tablet, gel, paste, bar, or flake. In a preferred embodiment of the present invention, the cleaning composition of the present invention comprises a laundry or dish detergent composition, which is in a single phase or multiphase unit dose form as encapsulated by a single compartment or multi-compartment water-soluble pouch, e.g., formed by a water-soluble polymer such as polyvinyl alcohol (PVA) or copolymers thereof. Preferably the composition is for manual-washing. Preferably, the cleaning composition of the present invention is a dishwashing detergent. Preferably the composition is in the form of a liquid.

As used herein, the term "laundry detergent" means a liquid or solid composition, and includes, unless otherwise indicated, granular or powder-form all-purpose or "heavy-duty" washing agents, especially cleaning detergents as well as cleaning auxiliaries such as bleach additives or pre-treat types. In a preferred embodiment of the present invention, the laundry detergent is a liquid laundry detergent composition. Preferably the composition is for manual-washing. Preferably the cleaning composition is a laundry detergent composition preferably for cleaning delicate fabrics.

As used herein the term "increased suds longevity" means an increase in the duration of visible suds in a washing process cleaning soiled articles using the composition comprising fatty acid decarboxylase enzyme, compared with the suds longevity provided by the same composition and process in the absence of the fatty acid decarboxylase enzyme.

As used herein, the term "soiled articles" refers non-specifically to any type of flexible material consisting of a network of natural or artificial fibers, including natural, artificial, and synthetic fibers, such as, but not limited to, cotton, linen, wool, polyester, nylon, silk, acrylic, and the like, as well as various blends and combinations. Soiled articles may further refer to any type of hard surface, including natural, artificial, or synthetic surfaces, such as, but not limited to, tile, granite, grout, glass, composite, vinyl, hardwood, metal, cooking surfaces, plastic, and the like, as well as blends and combinations, as well as dishware.

As used herein, the term "water hardness" or "hardness" means uncomplexed cations ion (i.e., $Ca^{2+}$ or $Mg^{2+}$) present in water that have the potential to precipitate under alkaline conditions, and thereby diminishing the surfactancy and cleaning capacity of surfactants. Further, the terms "high water hardness" and "elevated water hardness" can be used interchangeably and are relative terms for the purposes of the present invention, and are intended to include, but not limited to, a hardness level containing at least 12 grams of calcium ion per gallon water (gpg, "American grain hardness" units).

Fatty Acid Decarboxylase Enzyme

The fatty acid decarboxylase enzyme is preferably present in the composition in an amount from 0.00001 to 2 wt % based on the weight of the active protein. More preferably the fatty acid decarboxylase enzyme may be present in amounts from 0.0001 to 1 wt %, more preferably from 0.0005 to 0.5 wt %.

The term "fatty acid decarboxylase" or "a polypeptide having fatty acid decarboxylase activity" means an enzyme capable of catalyzing the elimination of the carboxyl group of a fatty acid. For the purposes of the present invention, fatty acid decarboxylase activity is defined by an enzyme or enzyme/cofactor/co-substrate system capable of catalyzing the conversion of any C10-20 saturated, monounsaturated or polyunsaturated fatty acid into its corresponding terminal alkene as shown in Scheme 1.

Scheme 1

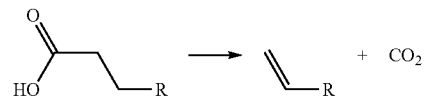

Suitable enzymes may be found in Cytochrome P450 families, although only a very small subset of Cytochrome P450 enzymes exhibit this activity. One example is the OleT$_{JE}$ enzyme endogenous to *Jeotgalicoccus* sp. 8456, and its variants. OleT$_{JE}$ binds strongly to a range of long chain fatty acids, and produces terminal alkenes from a wide variety of saturated fatty acids, using hydrogen peroxide as co-substrate. The amino acid sequence of OleT$_{JE}$ is given in SEQ ID NO: 1. Its properties are described in J. Belcher et al., *J. Biol. Chem.* (2014), 289, 10: 6535-6550. Variants of the enzyme with fused domains are capable of using molecular oxygen as co-substrate in the presence of an additional cofactor, as described by Y. Liu et al., *Biotechnol. Biofuels* (2014) 7: 28. OleT$_{JE}$ is a member of the Cytochrome P450 family CYP152 and is classified as CYP152L1. Related Cytochrome P450 enzymes may exhibit significant decarboxylase activity in line with OleT$_{JE}$ in wild-type form, yet others such as CYP152A1 and CYP152B1 are described as being more effective at catalyzing beta hydroxylation of fatty acids although protein engineering has been proven to convert such enzymes into more effective fatty acid decarboxylases, for example by making the Gln85His substitution in CYP152A1. Preferred fatty acid decarboxylase enzymes for use herein have at least 40% identity, preferably at least 50% or 60% or 65% or 70% or 75% or 80% or 85% of 90% or 95% or 96 or 97 or 98 or 99 or 100% identity to SEQ ID NO:1.

Other suitable enzymes are nonheme iron oxidase enzymes such as the UndA enzyme endogenous to *Pseudomonas* sp., as described by Z. Rui et al., *PNAS*, (2014), 111, 18237-18242. This is a member of the TENA/THI-4 protein family. The amino acid sequence of UndA is given in SEQ ID NO: 2. Preferred fatty acid decarboxylase enzymes for use herein have at least 40% identity, preferably at least 50% or 60% or 65% or 70% or 75% or 80% or 85% of 90% or 95% or 96 or 97 or 98 or 99 or 100% identity to SEQ ID NO:2.

A preferred fatty acid decarboxylase enzyme is active on unsaturated fatty acids having 10 to 20 carbon atoms, particularly oleic acid.

The fatty acid decarboxylase enzyme may be incorporated into the detergent composition via an additive particle, such as an enzyme granule or in the form of an encapsulate, or may be added in the form of a liquid formulation.

Suitable enzyme granules include: (i) spray-dried particles, (ii) layered particles in which the enzyme is coated as a layer around a pre-formed inert core, and fluid bed apparatus is used to adhere layers of coating material from aqueous solution containing coating materials, (iii) particles in which enzyme is absorbed into a core, (iv) extruded or pelletized enzyme particles in which an enzyme-containing paste is pressed into pellets or under pressure is extruded through orifices and cut into particles prior to drying; (v) prilled products in which an enzyme powder is suspended in molten wax and the suspension sprayed into a cooling chamber (e.g. through a rotating disc atomiser), (vi) agglomerated enzyme particles prepared by a process in which an enzyme-containing liquid is added to a dry powder composition comprising conventional granulating materials which may include e.g. fillers and binders optionally mixed with filaments such as cellulose fibres, or polymeric filaments such as polyvinyl pyrrolidone or polyvinyl alcohol filaments, to give extra strength and reduce dusting.

In particular when the cleaning composition comprises a liquid, it may be preferred to incorporate the enzyme via an encapsulate. Encapsulating the enzyme promotes the stability of the enzyme in the composition and helps to counteract the effect of any hostile compounds present in the composition, such as bleach, protease, surfactant, chelant, etc.

When in encapsulated form the enzymes are typically encapsulated in a polymeric material. Methods of encapsulation of the enzymes are for example, by spray-drying a liquid composition containing the enzyme(s) and the polymer(s), or by drying a liquid composition containing the enzyme and polymer, or by emulsion polymerisation, co-acervation, precipitation or interfacial polymerisation optionally in the presence of the enzyme, optionally followed by drying and/or size reduction processes. Suitable polymers for encapsulating enzymes include optionally modified: polyvinyl alcohol, polyvinylpyrrolidone, carboxymethylcellulose, guar gum, polycarboxylic acid, methylcellulose, hydroxypropyl methylcellulose, proteins, polybranched polyamines, such as polyethyleneimines (PEI), (hydrophobically modified) polysaccharide, a cellulosic polymer selected from the group consisting of, and mixtures thereof and derivatives or co-polymers thereof. Examples of modified cellulosic polymers include those mentioned above and in addition, hydroxypropyl methylcellulose phthalate, cellulose acetate phthalate Examples of modified gums include modified guar gum, gum benzoin, gum tragacanth, gum arabic and gum acacia. Examples of modified proteins are modified casein, gelatin and albumin. Examples of modified polymers may be selected from copolymers of at least one hydrophobic vinylic monomer with a least one hydrophilic vinylic monomer. Suitable hydrophilic vinylic monomer is vinylpyrrolidone. Suitable hydrophobic vinylic monomer is C1-C18 alkyl acrylates, C1-C18 alkyl methacrylates, C3-C18 cycloalkyl acrylates, C3-C18 cycloalkyl methacrylates and vinyl C1-C18 alkanoates and mixtures thereof. The polymer may comprise a polymer selected from homo- and copolymers having a C—C-backbone, wherein the C—C-backbone carries carboxyl groups, which may be present in the acidic form or in the neutralized form, and wherein the C—C-backbone comprises at least 20% by weight, e.g. from 20 to 98% by weight, based on the total weight of the polymer (i.e. based on the total weight of repeating units in the polymer P), of hydrophobic repeating units. The polymer may comprise branching, for example branched copolymer matrix particles formed from vinyl pyrrolidone and vinyl acetate. The polymer may comprise a copolymers, for example as described in WO2010/003934, based on maleic acid or (meth)acrylic acid. The polymer may be cross-linked.

Preferred polymers have a molecular weight from 1000 to 500,000, or 2000 to 200000 Dalton weight average. Typically the weight ratio of enzyme to polymer is from 1:50 to 10:1.

The polymer may be selected to be substantially soluble in an aqueous solution having an ionic strength of 0 mol/kg and insoluble in an aqueous solution having an ionic strength of more than 1 mol/kg according to method 1, for example as described in WO2008/084093, for example in which the polymer comprises 35-95% w/w of hydrophilic monomer units, based on the total weight of the polymer.

Hydrophobically modified polyvinyl alcohol or hydrophobically modified polyvinyl pyrrolidone may be preferred, optionally with high levels of hydrolysis, greater than 60%, or even greater than 80 or 90%. Suitable hydrophobic modifying groups include keto-ester and/or butyryl groups and mixtures thereof and preferably the total degree of substitution (DS) is between about 3% and 20%.

The fatty acid decarboxylase enzyme, when present in an additive particle may be the only enzyme in the additive particle or may be present in the additive particle in combination with one or more additional enzymes.

Suitable additional enzymes include protease such as metalloprotease or alkaline serine protease, such as subtilisin, amylase, lipase, cellulase, mannanase, pectinase, DNAse, oxidoreductase, peroxidases, lipases, phospholipases, cellobiohydrolases, cellobiose dehydrogenases, esterases, cutinases, pectinases, pectate lyases, keratinases, reductases, oxidases, phenoloxidases, lipoxygenases, ligninases, pullulanases, tannases, pentosanases, glucanases, arabinosidases, hyaluronidase, chondroitinase, laccases, amylases, oleate hydratases and mixtures thereof. In a preferred embodiment, the fatty acid decarboxylase enzyme may be incorporated into an additive particle in combination with an amylase, cellulase, protease and/or lipase enzyme, preferably a lipase or protease enzyme. Additional incorporation of oleate hydratase enzymes may also be preferred.

Surfactant System

The detergent typically comprises from about 1% to about 60%, preferably from about 5% to about 50% more preferably from about 8% to about 45% by weight thereof of a surfactant system. The surfactant system comprises one or more surfactants selected from the group consisting of anionic surfactants, cationic surfactants, nonionic surfactants, amphoteric surfactants, zwitterionic surfactants, and mixtures thereof. Preferably, the surfactants comprise an anionic surfactant selected from the group consisting of alkyl benzene sulfonate, alkoxylated alkyl sulfates, alkyl sulfates, and mixtures thereof.

A preferred surfactant system for providing food cleaning and good suds profile comprises i) an anionic surfactant; and ii) an amphoteric and/or zwitterionic surfactant. Preferably the weight ratio of anionic surfactant to amphoteric and/or zwitterionic surfactant is less than 9:1, more preferably less than 5:1 to about 1:2, more preferably from about 4:1 to about 1:1 and especially from about 4:1 to about 2:1

Extremely useful surfactant systems for use herein include those comprising anionic surfactants and comprising in addition, amine oxide and/or betaine surfactants. Amine oxide surfactants are particularly preferred. Preferably the surfactant system comprises an anionic surfactant selected from alkyl sulphate, alkyl alkoxy sulphate especially alkyl ethoxy sulphate, and mixtures thereof, in combination with amine oxide, most preferably in a weight % ratio of less than 9:1, more preferably less than 5:1 to about 1:2, more preferably from about 4:1 to about 1:1 and especially from about 4:1 to about 2:1.

Another preferred surfactant system for use herein comprises an anionic and amphoteric/zwitterionic system in which the amphoteric to zwitterionic weight ratio is preferably from about 2:1 to about 1:2. In particular a system in which the amphoteric surfactant comprises an amine oxide surfactant and the zwitteronic surfactant comprises a betaine. Preferred ratios of amine oxide to betaine are from 1.5:1 to 1:1.5, preferably from 1.2:1 to 1:1.2, most preferably about 1:1.

Also preferred for use herein are surfactant systems comprising non-ionic surfactants. Especially preferred surfactant systems for the composition of the invention comprise an anionic surfactant preferably selected from the group consisting of alkyl sulphate, alkyl alkoxy sulphate and mixtures thereof, more preferably an alkoxylated sulfate. Preferred surfactant systems comprise in addition an amphoteric surfactant, preferably an amine oxide surfactant. Preferred surfactant systems comprise a non-ionic surfactant. In summary, the most preferred surfactant system for use herein comprises an alkoxylated sulfate surfactant, amine oxide and non-ionic surfactant. Most preferably the nonionic surfactant is an alkoxylated alcohol surfactant, especially an ethoxylated alcohol surfactant.

Anionic Surfactant

Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, so as to form a water-soluble compound. Usually, the hydrophobic group will comprise a C 8-C 22 alkyl, and/or acyl group. Such surfactants are employed in the form of water-soluble salts and the salt-forming cation usually is selected from sodium, potassium, ammonium, magnesium and mono-, di- or tri-C 2-C 3 alkanolammonium, with the sodium, cation being the usual one chosen.

Preferably the surfactant system comprises an anionic surfactant or mixtures thereof. The anionic surfactant comprises any anionic cleaning surfactant, preferably selected from anionic sulphate or sulphonate surfactants or mixtures thereof.

Preferably the anionic surfactant is an alkoxylated alkyl sulphate surfactant, preferably an ethoxylated alkyl sulphate surfactant, preferably having an average ethoxylation degree of from about 0.2 to about 3, more preferably from about 0.3 to about 2, even more preferably from about 0.4 to about 1.5, and especially from about 0.4 to about 1. When the anionic surfactant is a mixture of surfactants, the alkoxylation degree is the weight average alkoxylation degree of all the components of the mixture (weight average alkoxylation degree). In the weight average alkoxylation degree calculation the weight of anionic surfactant components not having alkoxylated groups should also be included.

Weight average alkoxylation degree=
($x1$*alkoxylation degree of surfactant
1+$x2$*alkoxylation degree of surfactant
2+ . . . )/($x1$+$x2$+ . . . )

wherein $x1$, $x2$, . . . are the weights in grams of each anionic surfactant of the mixture and alkoxylation degree is the number of alkoxy groups in each anionic surfactant.

Also preferred are branched anionic surfactants, typically having a weight average level of branching of from 2 to 60% by weight, particularly those having a weight average level of branching of from about 5% to about 40%.

Preferably the anionic surfactant to be used in the detergent of the present invention comprises a branched anionic surfactant having a level of branching of from about 5% to about 40%, preferably from about 10 to about 35% and more preferably from about 20% to about 30%. Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the anionic surfactant used in the detergent of the invention. Most preferably the branched anionic surfactant is selected from alkyl sulphates, alkyl ethoxy sulphates, and mixtures thereof.

The branched anionic surfactant can be a single anionic surfactant or a mixture of anionic surfactants. In the case of a single surfactant the percentage of branching refers to the weight percentage of the hydrocarbyl chains that are branched in the original alcohol from which the surfactant is derived.

In the case of a surfactant mixture the percentage of branching is the weight average and it is defined according to the following formula:

Weight average of branching (%)=[($x1$*wt %
branched alcohol 1 in alcohol 1+$x2$*wt %
branched alcohol 2 in alcohol 2+ . . . )/
($x1$+$x2$+ . . . )]*100 wherein $x1$, $x2$, . . . are the weight in grams of each alcohol in the total alcohol mixture of the alcohols which were used as starting material for the anionic surfactant for the detergent of the invention. In the weight average branching degree calculation the weight of anionic surfactant components not having branched groups should also be included.

It may be preferred that the surfactant system comprises at least 50%, more preferably at least 60% and preferably at least 70% of branched anionic surfactant by weight of the surfactant system. In a particularly preferred surfactant system, the branched anionic surfactant comprises more than 50% by weight thereof of an alkyl ethoxylated sulphate having an ethoxylation degree of from about 0.1 to 5 or 0.2 to about 3 and preferably a level of branching of from about 5% to about 40%.

Preferably, the branched anionic surfactant comprises at least 50%, more preferably at least 60% and especially at least 70% of a sulphate surfactant by weight of the branched anionic surfactant. Especially preferred detergents from a cleaning view point art those in which the branched anionic surfactant comprises more than 50%, more preferably at least 60% and especially at least 70% by weight thereof of sulphate surfactant and the sulphate surfactant is selected from the group consisting of alkyl sulphate, alkyl ethoxy sulphates and mixtures thereof. Even more preferred are those in which the branched anionic surfactant has a degree of ethoxylation of from about 0.2 to about 3, more preferably from about 0.3 to about 2, even more preferably from about 0.4 to about 1.5, and especially from about 0.4 to about 1 and even more preferably when the anionic surfactant has a level of branching of from about 10% to about 35%, more preferably from about 20% to 30%.

Sulphate Surfactants

Preferably the surfactant comprises anionic sulphate surfactants. Anionic sulphate surfactants selected from the group consisting of alkyl sulphate, alkyl alkoxy sulphate and mixtures thereof may be particularly preferred, especially for dishwashing compositions.

Especially preferred are alkoxylated anionic surfactants, more preferably alkyl alkoxy sulphate surfactant. Preferred alkyl alkoxyl sulphates for use herein are alkyl ethoxy sulphates. Suitable sulphate surfactants for use herein include water-soluble salts of C8-C18 alkyl or hydroxyalkyl, sulphate and/or ether sulfate. Suitable counterions include alkali metal cation or ammonium or substituted ammonium, but preferably sodium.

The sulphate surfactants may be selected from C8-C18 primary, branched chain and random alkyl sulphates (AS); C8-C18 secondary (2,3) alkyl sulphates; C8-C18 alkyl alkoxy sulphates (AExS) wherein preferably x is from 1-30 in which the alkoxy group could be selected from ethoxy, propoxy, butoxy or even higher alkoxy groups and mixtures thereof. The alkoxylated anionic surfactant typically has an average alkoxylation degree of from about 0.1 to 11 or 0.1 to 7, preferably from about 0.2 to about 4, even more preferably from about 0.3 to about 3, even more preferably from about 0.4 to about 1.5 and especially from about 0.4 or 0.2 to about 1. Preferably, the alkoxy group is ethoxy.

Alkyl sulfates and alkyl alkoxy sulfates are commercially available with a variety of chain lengths, ethoxylation and branching degrees. Commercially available sulphates include, those based on Neodol alcohols ex the Shell company, Lial—Isalchem and Safol ex the Sasol company, natural alcohols ex The Procter & Gamble Chemicals company.

Preferably, the surfactant system comprises alkyl sulfates and/or alkyl ethoxy sulfates; more preferably a combination of alkyl sulfates and/or alkyl ethoxy sulfates with a combined average ethoxylation degree of less than 5, preferably less than 3, more preferably less than 2 and more than 0.5. Preferably the anionic surfactant has an average level of branching of from about 5% to about 40%.

Sulphonate Surfactants

Suitable sulphonate surfactants for use herein include water-soluble salts of C8-C18 alkyl or hydroxyalkyl sulphonates; C11-C18 alkyl benzene sulphonates (LAS), modified alkylbenzene sulphonate (MLAS); methyl ester sulphonate (MES); and alpha-olefin sulphonate (AOS). Those also include the paraffin sulphonates may be monosulphonates and/or disulphonates, obtained by sulphonating paraffins of 10 to 20 carbon atoms. The sulfonate surfactant also include the alkyl glyceryl sulphonate surfactants. In particular, for a laundry detergent the anionic surfactant preferably comprises at least 40% or more preferably at least 50% or at least 60% or even at least 80 or 90% sulphonate surfactant.

Fatty Acids

Water-soluble salts of the higher fatty acids, i.e., "soaps", may also be useful anionic surfactants in the cleaning compositions of the present invention, particularly for laundry detergents. However, the cleaning compositions of the present invention preferably contains soaps at a relatively low level, e.g., no more than about 3 wt %, more preferably not more than about 2 wt % or 1 wt %, and most preferably said cleaning composition is essentially free of soaps. Where fatty acids are added, they preferably contain very low levels of oleic acid. Levels of oleic acid in the composition are preferably below 0.5, more preferably below 0.3, more preferably below 0.2 or even below 0.1 wt % of the compositions, most preferably essentially free of oleic acid. Higher levels may be accommodated however, additional enzyme may need to be present to counteract the competition caused by their presence. Where oleic acid is incorporated, it may be preferred to also incorporate enzyme stabilizer. Physical stabilization such as by encapsulation may be particularly preferred.

Non-Ionic Surfactant

Nonionic surfactant, when present, are typically present in an amount of from 0.05% to 30%, preferably 0.1% to 20%, most preferably 0.5% to 10% or 0.5% to 7% or even 0.5% to 3% by weight of the composition. The nonionic surfactant is preferably present in the surfactant system in amounts from 1 to 60 wt % of the surfactant system, and particularly for laundry detergents preferably from 2 to 60, or 5 to 55 wt % based on the surfactant system. Suitable nonionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol. Highly preferred nonionic surfactants are the condensation products of Guerbet alcohols with from 2 to 18 moles, preferably 2 to 15, more preferably 5-12 of ethylene oxide per mole of alcohol.

However, in certain preferred embodiments of the present invention, particularly for dishwashing the cleaning composition contains nonionic surfactants at a relatively low level, e.g., no more than about 3 wt %, more preferably not more than about 2 wt % or 1 wt %, and most preferably said cleaning composition is essentially free of nonionic surfactants.

Other surfactants useful herein include amphoteric surfactants, zwitterionic surfactants and cationic surfactants. Such surfactants are typically present at levels from about 0.2 wt %, 0.5 wt % or 1 wt % to about 10 wt %, 20 wt % or 30 wt %. Preferably, the composition of the present invention will further comprise amphoteric and/or zwitterionic surfactant, more preferably an amine oxide and/or betaine surfactant, most preferably an amine oxide.

In a preferred but not necessary embodiment of the present invention, the cleaning composition is a liquid dish detergent composition containing from about 0.5 wt % to about 20 wt % of one or more amphoteric and/or zwitterionic surfactants, preferably amine oxide.

Amphoteric Surfactant

Preferred amphoteric surfactants are selected from the group consisting of amine oxide surfactants, such as, for example, alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one R1 C8-18 alkyl moiety and 2 R2 and R3 moieties selected from the group consisting of C1-3 alkyl groups and C1-3 hydroxyalkyl groups. Preferably amine oxide is characterized by the formula R1-N(R2)(R3) 0 wherein R1 is a C8-18 alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides. Preferred amine oxides include linear C10, linear C10-C12, and linear C12-C14 alkyl dimethyl amine oxides. As used herein "mid-branched" means that the amine oxide has one alkyl moiety having n1 carbon atoms with one alkyl branch on the alkyl moiety having n2 carbon atoms. The alkyl branch is located on the a carbon from the nitrogen on the alkyl moiety. This type of branching for the amine oxide is also known in the art as an internal amine oxide. The total sum of n1 and n2 is from 10 to 24 carbon atoms, preferably from 12 to 20, and more preferably from 10 to 16. The number of carbon atoms for the one alkyl moiety (n1) should be approximately the same number of carbon atoms as the one alkyl branch (n2) such that the one alkyl moiety and the one alkyl branch are symmetric. As used herein "symmetric" means that |n1-n2| is less than or equal to 5, preferably 4, most preferably from 0 to 4 carbon atoms in at least 50 wt %, more preferably at least 75 wt % to 100 wt % of the mid-branched amine oxides for use herein. The amine oxide further comprises two moieties independently selected from a C1-3 alkyl, a C1-3 hydroxyalkyl group, or a polyethylene oxide group containing an average of from about 1 to about 3 ethylene oxide groups. Preferably the two moieties are selected from a C1-3 alkyl, more preferably both are selected as a C1 alkyl. Most preferably the amine oxide is alkyl dimethyl amine oxide, especially C10-C18 alkyl dimethyl amine oxide.

Zwitterionic Surfactant

Other suitable surfactants include betaines, such as alkyl betaines, alkylamidobetaines, amidazoliniumbetaines, sulfobetaines (also referred to as INCI sultaines) as well as the phosphobetaines. Preferred betaines meet formula I:

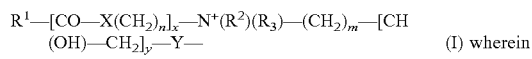
(I) wherein

R' is a saturated or unsaturated C6-22 alkyl residue, preferably C8-18 alkyl residue, in particular a saturated C10-16 alkyl residue, for example a saturated C12-14 alkyl residue;

X is NH, $NR^4$ with C1-4 Alkyl residue $R^4$, O or S, n a number from 1 to 10, preferably 2 to 5, in particular 3, x 0 or 1, preferably 1, $R^2$, $R^3$ are independently a C1-4 alkyl residue, potentially hydroxy substituted such as a hydroxyethyl, preferably a methyl.

m a number from 1 to 4, in particular 1, 2 or 3, y 0 or 1 and

Y is COO, SO3, $OPO(OR^5)O$ or $P(O)(OR^5)O$, whereby $R^5$ is a hydrogen atom H or a C1-4 alkyl residue.

Preferred betaines are the alkyl betaines of the formula (Ia), the alkyl amido propyl betaine of the formula (Ib), the sulfo betaines of the formula (Ic) and the amido sulfobetaines of the formula (Id);

(Ia)

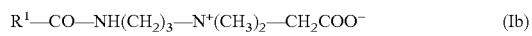
(Ib)

(Ic)

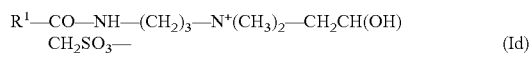
(Id)

in which $R^1$1 as the same meaning as in formula I. Particularly preferred betaines are the carbobetaines [wherein $Y^-=COO^-$], in particular the carbobetaines of the formula (Ia) and (Ib), more preferred are the alkylamidobetaines of the formula (Ib).

Examples of suitable betaines and sulfobetaines are the following [designated in accordance with INCI]: almondamidopropyl of betaines, apricotam idopropyl betaines, avocadamidopropyl of betaines, babassuamidopropyl of betaines, behenam idopropyl betaines, behenyl of betaines, betaines, canolam idopropyl betaines, capryl/capram idopropyl betaines, carnitine, cetyl of betaines, cocamidoethyl of betaines, cocam idopropyl betaines, cocam idopropyl hydroxysultaine, coco betaines, coco hydroxysultaine, coco/oleam idopropyl betaines, coco sultaine, decyl of betaines, dihydroxyethyl oleyl glycinate, dihydroxyethyl soy glycinate, dihydroxyethyl stearyl glycinate, dihydroxyethyl tallow glycinate, dimethicone propyl of PG-betaines, erucam idopropyl hydroxysultaine, hydrogenated tallow of betaines, isostearam idopropyl betaines, lauram idopropyl betaines, lauryl of betaines, lauryl hydroxysultaine, lauryl sultaine, milkam idopropyl betaines, minkamidopropyl of betaines, myristam idopropyl betaines, myristyl of betaines, oleam idopropyl betaines, oleam idopropyl hydroxysultaine, oleyl of betaines, olivamidopropyl of betaines, palmam idopropyl betaines, palm itam idopropyl betaines, palmitoyl Carnitine, palm kernelam idopropyl betaines, polytetrafluoroethylene acetoxypropyl of betaines, ricinoleam idopropyl betaines, sesam idopropyl betaines, soyam idopropyl betaines, stearam idopropyl betaines, stearyl of betaines, tallowam idopropyl betaines, tallowam idopropyl hydroxysultaine, tallow of betaines, tallow dihydroxyethyl of betaines, undecylenam idopropyl betaines and wheat germam idopropyl betaines. A preferred betaine is, for example, cocoamidopropylbetaine.

The most preferred surfactant system particularly for a dishwashing detergent composition of the present invention comprises: (i) 1% to 40%, preferably 6% to 32%, more preferably 8% to 25% weight of the total composition of an anionic surfactant, preferably comprising an alkoxylated sulfate surfactant (ii) 0.01% to 20% wt, preferably from 0.2% to 15% wt, more preferably from 0.5% to 10% by weight of the composition of amphoteric and/or zwitterionic and/or nonionic surfactant. Preferred compositions comprise 0.01% to 20 wt % of the composition of amphoteric and nonionic surfactant, most preferably wherein the amphoteric surfactant comprises amine oxide surfactant. It has been found that such surfactant system in combination with the fatty acid decarboxylase enzyme will provide the excellent cleaning required from a washing detergent while having very good suds profile, especially in the presence of greasy soils and break-down products of greasy soils, and provides a good finish of the washed items.

Enzyme Stabilizer

Preferably the composition of the invention comprises an enzyme stabilizer. Suitable enzyme stabilizers may be selected from the group consisting of (a) univalent, bivalent and/or trivalent cations preferably selected from the group of inorganic or organic salts of alkaline earth metals, alkali metals, aluminum, iron, copper and zinc, preferably alkali metals and alkaline earth metals, preferably alkali metal and alkaline earth metal salts with halides, sulfates, sulfites, carbonates, hydrogencarbonates, nitrates, nitrites, phosphates, formates, acetates, propionates, citrates, maleates, tartrates, succinates, oxalates, lactates, and mixtures thereof. In a preferred embodiment the salt is selected from the group consisting of sodium chloride, calcium chloride, potassium chloride, sodium sulfate, potassium sulfate, sodium acetate, potassium acetate, sodium formate, potassium formate, calcium lactate, calcium nitrate and mixtures thereof. Most preferred are salts selected from the group consisting of calcium chloride, potassium chloride, potassium sulfate, sodium acetate, potassium acetate, sodium formate, potassium formate, calcium lactate, calcium nitrate, and mixtures thereof, and in particular potassium salts selected from the group of potassium chloride, potassium sulfate, potassium acetate, potassium formate, potassium propionate, potassium lactate and mixtures thereof. Most preferred are potassium acetate and potassium chloride. Preferred calcium salts are calcium formate, calcium lactate and calcium nitrate including calcium nitrate tetrahydrate. Calcium and sodium formate salts may be preferred. These cations are present at at least about 0.01 wt %, preferably at least about 0.03 wt %, more preferably at least about 0.05 wt %, most preferably at least about 0.25 wt % up to about 2 wt % or even up to about 1 wt % by weight of the total composition. These salts are formulated from about 0.1 to about 5 wt %, preferably from about 0.2 to about 4 wt %, more preferably from about 0.3 to about 3 wt %, most preferably from about 0.5 to about 2 wt % relative to the total weight of the composition. Further enzyme stabilizers can be selected from the group (b) carbohydrates selected from the group consisting of oligosaccharides, polysaccharides and mixtures thereof, such as a monosaccharide glycerate; (c) mass efficient reversible protease inhibitors selected from the group consisting of phenyl boronic acid and derivatives thereof, preferably 4-formyl phenylboronic acid; (d) alcohols such as 1,2-propane diol, propylene glycol; (e) peptide aldehyde stabilizers such as tripeptide aldehydes such as Cbz-Gly-Ala-Tyr-H, or disubstituted alaninamide; (f) carboxylic acids such as phenyl alkyl dicarboxylic acid or multiply substituted benzyl carboxylic acid comprising a carboxyl group on at least two carbon atoms of the benzyl radical, phthaloyl glutamine acid, phthaloyl asparagine acid, aminophthalic acid and/or an oligoamino-biphenyl-oligocarboxylic acid; and; (g) mixtures thereof. An example of a suitable mixture comprises: (1) reversible protease inhibitors such as a boron containing compound; (2) 1-2 propane diol; (3) calcium formate and/or sodium formate; and (4) any combination thereof.

If the cleaning composition of the present invention is provided in a powder form, it may also be especially preferred for the powder to comprise low levels, or even be essentially free, of builder. The term "essentially free" means that the composition "comprises no deliberately added" amount of that ingredient. In a preferred embodiment, the cleaning composition of the present invention comprises no builder.

Source of Hydrogen Peroxide

It may be preferred for the composition to comprise a source of hydrogen peroxide. Sources of hydrogen peroxide include, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. Percarbonate salts are preferred. When employed, inorganic perhydrate salts are typically present in amounts of from 0.05 to 40 wt %, or 1 to 30 wt % of the overall fabric and home care product and are typically incorporated into such fabric and home care products as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps. These may be present in combination with bleach activators and/or bleach catalysts.

Suitable bleach activators are those having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). While any suitable bleach activator may be employed, it may be preferred if the subject composition comprises NOBS, TAED or mixtures thereof.

Suitable bleach catalysts include one or more bleach catalysts capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and alpha amino-ketones and mixtures thereof.

Suitable bleach catalysts include oxaziridinium bleach catalysts, transition metal bleach catalysts, especially manganese and iron bleach catalysts. A suitable bleach catalyst has a structure corresponding to general formula below:

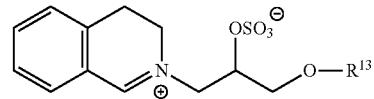

wherein $R^{13}$ is selected from the group consisting of 2-ethylhexyl, 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl.

Another suitable source of hydrogen peroxide includes pre-formed peracids. Suitable preformed peracids include, but are not limited to compounds selected from the group consisting of pre-formed peroxyacids or salts thereof typically a percarboxylic acids and salts, percarbonic acids and salts, perimidic acids and salts, peroxymonosulfuric acids and salts, for example, Oxone®, and mixtures thereof. Suitable examples include peroxycarboxylic acids or salts thereof, or peroxysulphonic acids or salts thereof. Typical peroxycarboxylic acid salts suitable for use herein have a chemical structure corresponding to the following chemical formula:

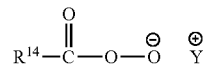

wherein: $R^{14}$ is selected from alkyl, aralkyl, cycloalkyl, aryl or heterocyclic groups; the $R^{14}$ group can be linear or branched, substituted or unsubstituted; having, when the peracid is hydrophobic, from 6 to 14 carbon atoms, or from 8 to 12 carbon atoms and, when the peracid is hydrophilic, less than 6 carbon atoms or even less than 4 carbon atoms and Y is any suitable counter-ion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Particularly preferred peroxyacids are phthalimido-peroxy-alkanoic acids, in particular ε-phthalimido peroxy hexanoic acid (PAP). Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

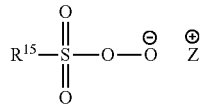

wherein: $R^{15}$ is selected from alkyl, aralkyl, cycloalkyl, aryl or heterocyclic groups; the R'5 group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{4-14}$, preferably $C_{6-14}$ alkyl. Preferably such bleach components may be present in the compositions of the invention in an amount from 0.01 to 50%, most preferably from 0.1% to 20%.

Hydrogen peroxide may also be provided by the incorporation of a carbohydrate oxidase enzyme. This will react in situ in the washing process with carbohydrates either from the soil or from a substrate also present in the composition, to generate hydrogen peroxide. Since this will tend to generate low levels of hydrogen peroxide this may be preferred.

Additional Enzymes

Suitable additional enzymes include protease such as metalloprotease or alkaline serine protease, such as subtilisin, amylase, lipase, cellulase, mannanase, pectinase, DNAse, oxidoreductase, peroxidases, lipases, phospholipases, cellobiohydrolases, cellobiose dehydrogenases, esterases, cutinases, pectinases, pectate lyases, keratinases, reductases, oxidases, phenoloxidases, lipoxygenases, ligninases, pullulanases, tannases, pentosanases, glucanases, arabinosidases, hyaluronidase, chondroitinase, laccases, amylases, oleate hydratases and mixtures thereof.

Preferred compositions of the invention comprise one or more enzymes selected from lipases, proteases, cellulases, amylases and any combination thereof.

Each additional enzyme is typically present in an amount from 0.0001 to 1 wt % (weight of active protein) more preferably from 0.0005 to 0.5 wt %, most preferably 0.005-0.1%). It may be particularly preferred for the compositions of the present invention to additionally comprise a lipase enzyme. Lipases break down fatty ester soils into fatty acids which are then acted upon by the fatty acid decarboxylase enzyme into suds neutral or suds boosting agents. Suitable lipases include those of bacterial, fungal or synthetic origin, and variants thereof. Chemically modified or protein engineered mutants are also suitable. Examples of suitable lipases include lipases from *Humicola* (synonym *Thermomyces*), e.g., from *H. lanuginosa* (*T. lanuginosus*).

The lipase may be a "first cycle lipase", e.g. such as those described in WO06/090335 and WO13/116261. In one aspect, the lipase is a first-wash lipase, preferably a variant of the wild-type lipase from *Thermomyces lanuginosus* comprising T231R and/or N233R mutations. Preferred lipases include those sold under the tradenames Lipex®, Lipolex® and Lipoclean® by Novozymes, Bagsvaerd, Denmark.

Other suitable lipases include: Liprl 139 and TfuLip2.

It may be particularly preferred for the compositions of the present invention to additionally comprise a protease enzyme. Since oleic acid and other foam suppressing fatty acids are present in body soils or even human skin, as protease enzyme acts as a skin care agent, or breaks down proteinaceous soils, fatty acids released are consequently broken down by the fatty acid decarboxylase, preventing suds suppression accordingly. Suitable proteases include metalloproteases and/or serine proteases. Examples of suitable neutral or alkaline proteases include: subtilisins (EC 3.4.21.62); trypsin-type or chymotrypsin-type proteases; and metalloproteases. The suitable proteases include chemically or genetically modified mutants of the aforementioned suitable proteases.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Preferenz P® series of proteases including Preferenz® P280, Preferenz® P281, Preferenz® P2018-C, Preferenz® P2081-WE, Preferenz® P2082-EE and Preferenz® P2083-A/J, Properase®, Purafect®, Purafect Prime®, Purafect Ox®, FN3®, FN4®, Excellase® and Purafect OXP® by DuPont, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (*Bacillus alkalophilus* subtilisin with mutations A230V+S256G+S259N) from Kao.

It may be particularly preferred for the compositions of the present invention to additionally comprise an amylase enzyme. Since oily soils are commonly entrapped in starchy soils, the amylase and fatty acid decarboxylase enzymes work synergistically together: fatty acid soils are released by breakdown of starchy soils with amylase, thus, the fatty acid decarboxylase enzyme is particularly effective in ensuring there is no negative impact on suds in the wash liquor. Preferred amylases are derived from AA560 alpha amylase endogenous to *Bacillus* sp. DSM 12649, preferably having the following mutations: R118K, D183*, G184*, N195F, R320K, and/or R458K. Suitable commercially available amylases include Stainzyme®, Stainzyme® Plus, Natalase, Termamyl®, Termamyl® Ultra, Liquezyme® SZ, Duramyl®, Everest® (all Novozymes) and Spezyme® AA, Preferenz S® series of amylases, Purastar® and Purastar® Ox Am, Optisize® HT Plus (all Du Pont). A suitable amylase is described in WO06/002643.

It may be particularly preferred for the compositions of the present invention to additionally comprise a cellulase enzyme. Suitable cellulases include those of bacterial or fungal origin. Chemically modified or protein engineered mutants are also suitable. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum*.

Commercially available cellulases include Celluzyme®, Carezyme®, and Carezyme® Premium, Celluclean® and Whitezyme® (Novozymes A/S), Revitalenz® series of enzymes (Du Pont), and Biotouch® series of enzymes (AB Enzymes). Suitable commercially available cellulases include Carezyme® Premium, Celluclean® Classic.

It may be particularly preferred for the compositions of the present invention to additionally comprise an oleate hydratase enzyme. Suitable oleate hydratases may be selected from E.C. classification numbers 1.11.2.3 (plant seed peroxygenase), 1.13.11.77 (oleate 10S lipoxygenase), 3.1.2.14 (oleoyl-[acyl-carrier-protein] hydrolase, 3.5.1.99 (fatty acid amide hydrolase), 4.2.1.53 (oleate hydratase) and mixtures thereof. Where necessary, the composition comprises, provides access to or forms in situ any additional substrate necessary for the effective functioning of the enzyme: hydroperoxide for plant seed peroxygenase; oxygen for oleate 10S lipoxygenase; thiol for oleoyl-[acyl-carrier-protein] hydrolase; ammonia or amines for fatty acid hydrolase; water for oleate hydratase. Preferably the oleic acid-transforming enzyme is an oleate hydratase from class EC 4.2.1.53. Suitable oleate hydratases include the wild-types oleate hydratases listed in Table 1 and variants thereof which exhibit oleate hydratase activity.

TABLE 1

| Origin |
| --- |
| *Elizabethkingia meningoseptica* |
| *Lysinibacillus fusiformis* |
| *Macrococcus caseolyticus* |
| *Lactobacillus acidophilus* |
| *Stenotrophomonas maltophilia* |
| *Streptococcus pyogenes* |
| *Bifidobacterium breve* |
| *Bifidobacterium animalis* subsp. *lactis* (strain BB-12) |
| *Lactobacillus plantarum* subsp. *plantarum* ST-III |
| *Lactobacillus rhamnosus* LGG |
| *Lactobacillus casei* W56 |
| *Lactobacillus delbrueckii* subsp. *bulgaricus* |

Chelant

The detergent composition herein typically comprises a chelant at a level of from 0.1% to 20%, preferably from 0.2% to 5%, more preferably from 0.2% to 3% by weight of total composition.

As commonly understood in the detergent field, chelation herein means the binding or complexation of a bi- or multidentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates or scale, or forming encrustations on soils turning them harder to be removed. The ligand forms a chelate complex with the substrate. The term is reserved for complexes in which the metal ion is bound to two or more atoms of the chelant.

Suitable chelating agents can be selected from the group consisting of amino carboxylates, amino phosphonates, polycarboxylate chelating agents and mixtures thereof.

Preferred chelants for use herein are the amino acids based chelants and preferably glutamic-N,N-diacetic acid (GLDA), methylglycine-N,N-diacetic acid (MGDA), and derivatives, and/or phosphonate based chelants and preferably diethylenetriamine penta methylphosphonic acid or hydroxyethyldiphosphonic acid. GLDA (salts and derivatives thereof) is especially preferred according to the invention, with the tetrasodium salt thereof being especially preferred.

Other chelants include homopolymers and copolymers of polycarboxylic acids and their partially or completely neutralized salts, monomeric polycarboxylic acids and hydroxycarboxylic acids and their salts. Suitable polycarboxylic acids are acyclic, alicyclic, heterocyclic and aromatic carboxylic acids, in which case they contain at least two carboxyl groups which are in each case separated from one another by, preferably, no more than two carbon atoms. A suitable hydroxycarboxylic acid is, for example, citric acid. Another suitable polycarboxylic acid is the homopolymer of acrylic acid. Preferred are the polycarboxylates end capped with sulfonates.

Solvents

When the cleaning composition is in the form of a liquid detergent composition, particularly a laundry or liquid dishwashing detergent it may further comprise one or more organic solvents, which can be present in an amount ranging from about 1 wt % to about 80 wt %, preferably 5 wt % to about 70 wt %, more preferably from about 10 wt % to about 60 wt %, even more preferably from about 15 wt % to about 50 wt %, and most preferably from about 20 wt % to about 45 wt %, by total weight of the composition. Preferably the composition comprises cleaning solvents, especially when the composition is a dishwashing composition.

Cleaning Solvents

The liquid compositions of the present invention may comprise a grease cleaning solvent, or mixtures thereof as a highly preferred optional ingredient. Suitable solvent is selected from the group consisting of: ethers and diethers having from 4 to 14 carbon atoms, preferably from 6 to 12 carbon atoms, and more preferably from 8 to 10 carbon atoms; glycols or alkoxylated glycols; alkoxylated aromatic alcohols; aromatic alcohols; alkoxylated aliphatic alcohols; aliphatic alcohols; C8-C14 alkyl and cycloalkyl hydrocarbons and halohydrocarbons; C6-C16 glycol ethers; alkanolamines; terpenes and mixtures thereof. Typically, the liquid composition herein may comprise up to 30%, preferably from 1% to 25%, more preferably from 1% to 20% and most preferably from 2% to 10% by weight of the total composition of said solvent or mixture thereof.

Because phase separation is a constant challenge for liquid detergent compositions, especially when the salt content in such compositions is high, the solvent system of the present invention is particularly designed to minimize the risk of phase separation. Specifically, the solvent system of the present invention is composed mostly of diols, such as ethylene glycol, diethylene glycol, propylene glycol, dipropylene glycol, butylene glycol, pentanediols, and combinations thereof. The diols are present in the liquid detergent composition of the present invention in a total amount ranging from about 2 wt % to about 50 wt %. Preferably, the composition contains ethylene, diethylene glycol, and/or propylene glycol in a total amount ranging from about 5 wt % to about 40 wt %. More preferably, the composition contains propylene glycol in the amount ranging from about 15 wt % to about 35 wt %. Other organic solvents may also be present, which include, but are not limited to: methanol, ethanol, glycerin, sodium cumene sulfonate, potassium cumene sulfonate, ammonium cumene sulfonate, sodium toluene sulfonate, potassium toluene sulfonate, sodium xylene sulfonate, potassium xylene sulfonate, ammonium xylene sulfonate, or mixtures thereof. Other lower alcohols, such $C_1$-$C_4$ alkanolamines, e.g., monoethanolamine and/or triethanolamine, may also be used. In a particularly preferred embodiment of the present invention, the liquid detergent compositions of the present invention also contain from about 5 wt % to about 20 wt %, preferably from 6 wt % to 18 wt %, more preferably from 8 wt % to 16 wt % of glycerin in addition to the diol(s).

The liquid detergent composition of the present invention preferably contains water in combination with the above-mentioned organic solvent(s) as carrier(s). In some embodiments, water is present in the liquid detergent compositions of the present invention in the amount ranging from about 20 wt % to about 90 wt %, preferably from about 25 wt % to 80 wt %, and more preferably from about 30 wt % to about 70 wt %. In other embodiments, water is absent and the composition is anhydrous. Highly preferred compositions afforded by the present invention are clear, isotropic liquids.

The liquid detergent composition as described herein above may also contain an external structurant, which may be present in an amount ranging from about 0.001% to about 1.0%, preferably from about 0.05% to about 0.5%, more preferably from about 0.1% to about 0.3% by total weight of the composition. Particularly preferred external structurants for the practice of the present invention are selected from hydrogenated castor oil, which is also referred to as trihydroxylstearin and is commercially available under the tradename Thixin®, and optionally modified natural fibres such as citrus fibres.

The balance of the cleaning composition of the present invention typically contains from about 5 wt % to about 70 wt %, or about 10 wt % to about 60 wt % adjunct ingredients.

Suitable adjunct ingredients for laundry detergent products include: builders, chelating agents, dye transfer inhibiting agents, dispersants, rheology modifiers, catalytic materials, bleach activators, hydrogen peroxide, sources of hydrogen peroxide, preformed peracids, polymeric dispersing agents, clay soil removal/anti-redeposition agents, brighteners, suds suppressors, dyes, photobleaches, structure elasticizing agents, fabric softeners, carriers, hydrotropes, processing aids, solvents, hueing agents, anti-microbial agents, free perfume oils, pungent agents, aversive agents, emetic agents, bittering agents and/or pigments. The precise nature of these adjunct ingredients and the levels thereof in the liquid laundry detergent composition will depend on factors like the specific type of the composition and the nature of the cleaning operation for which it is to be used.

Suitable adjunct ingredients for dish detergent products include: builders, chelants, conditioning polymers, cleaning polymers, surface modifying polymers, soil flocculating polymers, structurants, emollients, humectants, skin rejuvenating actives, carboxylic acids, scrubbing particles, bleach and bleach activators, perfumes, malodor control agents, pigments, dyes, opacifiers, beads, pearlescent particles, microcapsules, organic and inorganic cations such as alkaline earth metals such as Ca/Mg-ions and diamines, antibacterial agents, preservatives and pH adjusters and buffering means.

When the composition comprises a solid free-flowing particulate detergent composition preferably comprises a fully formulated laundry detergent composition, not a portion thereof such as a spray-dried, extruded or agglomerate particle that only forms part of the laundry detergent composition. Typically, the solid composition comprises a plurality of chemically different particles, such as spray-dried base detergent particles and/or agglomerated base detergent particles and/or extruded base detergent particles, in combination with one or more, typically two or more, or five or more, or even ten or more particles selected from: surfactant particles, including surfactant agglomerates, surfactant extrudates, surfactant needles, surfactant noodles, surfactant flakes; phosphate particles; zeolite particles; silicate salt particles, especially sodium silicate particles; carbonate salt particles, especially sodium carbonate particles; polymer particles such as carboxylate polymer particles, cellulosic polymer particles, starch particles, polyester particles, polyamine particles, terephthalate polymer particles, polyethylene glycol particles; aesthetic particles such as coloured noodles, needles, lamellae particles and ring particles; enzyme particles such as protease granulates, amylase granulates, lipase granulates, cellulase granulates, mannanase granulates, pectate lyase granulates, xyloglucanase granulates, bleaching enzyme granulates and co-granulates of any of these enzymes, preferably these enzyme granulates comprise sodium sulphate; bleach particles, such as percarbonate particles, especially coated percarbonate particles, such as percarbonate coated with carbonate salt, sulphate salt, silicate salt, borosilicate salt, or any combination thereof, perborate particles, bleach activator particles such as tetra acetyl ethylene diamine particles and/or alkyl oxybenzene sulphonate particles, bleach catalyst particles such as transition metal catalyst particles, and/or isoquinolinium bleach catalyst particles, pre-formed peracid particles, especially coated pre-formed peracid particles; filler particles such as sulphate salt particles and chloride particles; clay particles such as montmorillonite particles and particles of clay and silicone; flocculant particles such as polyethylene oxide particles; wax particles such as wax agglomerates; silicone particles, brightener particles; dye transfer inhibition particles; dye fixative particles; perfume particles such as perfume microcapsules and starch encapsulated perfume accord particles, or pro-perfume particles such as Schiff base reaction product particles; hueing dye particles; chelant particles such as chelant agglomerates; and any combination thereof.

Polymers

Carboxylate Polymer:

The composition may comprise a carboxylate polymer, such as a maleate/acrylate random copolymer or polyacrylate homopolymer. Suitable carboxylate polymers include: polyacrylate homopolymers having a molecular weight of from 4,000 Da to 9,000 Da; maleate/acrylate random copolymers having a molecular weight of from 50,000 Da to 100,000 Da, or from 60,000 Da to 80,000 Da.

Another suitable carboxylate polymer is a co-polymer that comprises: (i) from 50 to less than 98 wt % structural units derived from one or more monomers comprising carboxyl groups; (ii) from 1 to less than 49 wt % structural units derived from one or more monomers comprising sulfonate moieties; and (iii) from 1 to 49 wt % structural units derived from one or more types of monomers selected from ether bond-containing monomers represented by formulas (I) and (II):

formula (I)

wherein in formula (I), $R_0$ represents a hydrogen atom or $CH_3$ group, R represents a $CH_2$ group, $CH_2CH_2$ group or single bond, X represents a number 0-5 provided X represents a number 1-5 when R is a single bond, and $R_1$ is a hydrogen atom or $C_1$ to $C_{20}$ organic group;

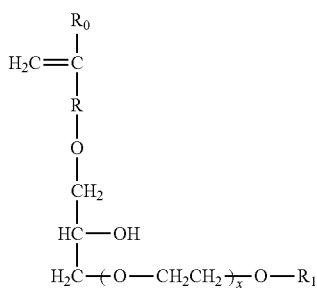

formula (II)

wherein in formula (II), $R_0$ represents a hydrogen atom or $CH_3$ group, R represents a $CH_2$ group, $CH_2CH_2$ group or single bond, X represents a number 0-5, and $R_1$ is a hydrogen atom or $C_1$ to $C_{20}$ organic group.

It may be preferred that the polymer has a weight average molecular weight of at least 50 kDa, or even at least 70 kDa.

Soil Release Polymer:

The composition may comprise a soil release polymer. A suitable soil release polymer has a structure as defined by one of the following structures (I), (II) or (III):

$$—[(OCHR^1—CHR^2)_a—O—OC—Ar—CO-]_d \quad (I)$$

$$—[(OCHR^3—CHR^4)_b—O—OC\text{-}sAr\text{-}CO\text{-}]_e \quad (II)$$

$$—[(OCHR^5—CHR^6)_c—OR^7]_f \quad (III)$$

wherein:
a, b and c are from 1 to 200;
d, e and f are from 1 to 50;
Ar is a 1,4-substituted phenylene;
sAr is 1,3-substituted phenylene substituted in position 5 with $SO_3$Me;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are sold by Clariant under the TexCare® series of polymers, e.g. TexCare® SRN240 and TexCare® SRA300. Other suitable soil release polymers are sold by Solvay under the Repel-o-Tex® series of polymers, e.g. Repel-o-Tex® SF2 and Repel-o-Tex® Crystal.

Anti-Redeposition Polymer:

Suitable anti-redeposition polymers include polyethylene glycol polymers and/or polyethyleneimine polymers.

Suitable polyethylene glycol polymers include random graft co-polymers comprising: (i) hydrophilic backbone comprising polyethylene glycol; and (ii) hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22.

Cellulosic Polymer:

Suitable cellulosic polymers are selected from alkyl cellulose, alkyl alkoxyalkyl cellulose, carboxyalkyl cellulose, alkyl carboxyalkyl cellulose, sulphoalkyl cellulose, more preferably selected from carboxymethyl cellulose, methyl cellulose, methyl hydroxyethyl cellulose, methyl carboxymethyl cellulose, and mixtures thereof.

Suitable carboxymethyl celluloses have a degree of carboxymethyl substitution from 0.5 to 0.9 and a molecular weight from 100,000 Da to 300,000 Da.

Suitable carboxymethyl celluloses have a degree of substitution greater than 0.65 and a degree of blockiness greater than 0.45.

Care Polymers:

Suitable care polymers include cellulosic polymers that are cationically modified or hydrophobically modified. Such modified cellulosic polymers can provide anti-abrasion benefits and dye lock benefits to fabric during the laundering cycle. Suitable cellulosic polymers include cationically modified hydroxyethyl cellulose.

Other suitable care polymers include dye lock polymers, for example the condensation oligomer produced by the condensation of imidazole and epichlorhydrin, preferably in ratio of 1:4:1. A suitable commercially available dye lock polymer is Polyquart® FDI (Cognis).

Other suitable care polymers include amino-silicone, which can provide fabric feel benefits and fabric shape retention benefits.

Bleach:

Suitable bleach includes sources of hydrogen peroxide, bleach activators, bleach catalysts, pre-formed peracids and any combination thereof. A particularly suitable bleach includes a combination of a source of hydrogen peroxide with a bleach activator and/or a bleach catalyst.

Brightener:

Suitable fluorescent brighteners include: di-styryl biphenyl compounds, e.g. Tinopal® CBS-X, di-amino stilbene di-sulfonic acid compounds, e.g. Tinopal® DMS pure Xtra and Blankophor® HRH, and Pyrazoline compounds, e.g. Blankophor® SN, and coumarin compounds, e.g. Tinopal® SWN.

Preferred brighteners are: sodium 2 (4-styryl-3-sulfophenyl)-2H-napthol[1,2-d]triazole, disodium 4,4'-bis{[(4-anilino-6-(N methyl-N-2 hydroxyethyl)amino 1,3,5-triazin-2-yl)];amino}stilbene-2-2' disulfonate, disodium 4,4'-bis{[(4-anilino-6-morpholino-1,3,5-triazin-2-yl)]amino} stilbene-2-2' disulfonate, and disodium 4,4'-bis(2-sulfostyryl)biphenyl. A suitable fluorescent brightener is C.I. Fluorescent Brightener 260, which may be used in its beta or alpha crystalline forms, or a mixture of these forms.

Hueing Agent:

Suitable hueing agents include small molecule dyes, typically falling into the Colour Index (C.I.) classifications of Acid, Direct, Basic, Reactive (including hydrolysed forms thereof) or Solvent or Disperse dyes, for example classified as Blue, Violet, Red, Green or Black, and provide the desired shade either alone or in combination. Preferred such hueing agents include Acid Violet 50, Direct Violet 9, 66 and 99, Solvent Violet 13 and any combination thereof.

Many hueing agents are known and described in the art which may be suitable for the present invention. Suitable hueing agents include phthalocyanine and azo dye conjugates. Suitable hueing agents may be alkoxylated. Such alkoxylated compounds may be produced by organic synthesis that may produce a mixture of molecules having different degrees of alkoxylation. Such mixtures may be used directly to provide the hueing agent, or may undergo a purification step to increase the proportion of the target molecule. Suitable hueing agents include alkoxylated bis-azo dyes.

The hueing agent may be incorporated into the detergent composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route. Suitable hueing agents can be incorporated into hueing dye particles.

Dye Transfer Inhibitors:

Suitable dye transfer inhibitors include polyamine N-oxide polymers, copolymers of N-vinylpyrrolidone and N-vinylimidazole, polyvinylpyrrolidone, polyvinyloxazolidone, polyvinylimidazole and mixtures thereof. Preferred are poly (vinyl pyrrolidone), poly(vinylpyridine betaine), poly(vinylpyridine N-oxide), poly(vinyl pyrrolidone-vinyl imidazole) and mixtures thereof. Suitable commercially available dye transfer inhibitors include PVP-K15 and K30 (Ashland), Sokalan® HP165, HP50, HP53, HP59, HP56K, HP56, HP66 (BASF), Chromabond® S-400, S403E and S-100 (Ashland).

Perfume:

Suitable perfumes comprise perfume materials selected from the group: (a) perfume materials having a C log P of less than 3.0 and a boiling point of less than 250° C. (quadrant 1 perfume materials); (b) perfume materials having a C log P of less than 3.0 and a boiling point of 250° C. or greater (quadrant 2 perfume materials); (c) perfume materials having a C log P of 3.0 or greater and a boiling point of less than 250° C. (quadrant 3 perfume materials); (d) perfume materials having a C log P of 3.0 or greater and a boiling point of 250° C. or greater (quadrant 4 perfume materials); and (e) mixtures thereof.

It may be preferred for the perfume to be in the form of a perfume delivery technology. Such delivery technologies further stabilize and enhance the deposition and release of perfume materials from the laundered fabric. Such perfume delivery technologies can also be used to further increase the longevity of perfume release from the laundered fabric. Suitable perfume delivery technologies include: perfume microcapsules, pro-perfumes, polymer assisted deliveries, molecule assisted deliveries, fiber assisted deliveries, amine assisted deliveries, cyclodextrin, starch encapsulated accord, zeolite and other inorganic carriers, and any mixture thereof.

A preferred detergent composition is preferably a manual dishwashing detergent, preferably in liquid form. It typically contains from 30% to 95%, preferably from 40% to 90%, more preferably from 50% to 85% by weight of a liquid carrier in which the other essential and optional components are dissolved, dispersed or suspended. One preferred component of the liquid carrier is water.

Preferably the pH of the detergent is adjusted to between 3 and 14, more preferably between 4 and 13, more preferably between 6 and 12 and most preferably between 8 and 10. The pH of the detergent can be adjusted using pH modifying ingredients known in the art.

Method of Washing

Other aspects of the invention are directed to methods of washing ware especially dishware with the composition of the present invention. Said methods comprise the step of applying the composition, preferably in liquid form, onto the soiled articles especially dishware surface, either in diluted or neat form and rinsing or leaving the composition to dry on the surface without rinsing the surface.

By "in its neat form", it is meant herein that said composition is applied directly onto the surface to be treated and/or onto a cleaning device or implement such as a pre-treat device, dish cloth, a sponge or a dish brush without undergoing any dilution (immediately) prior to the application. The cleaning device or implement is preferably wet before or after the composition is delivered to it. By "diluted form", it is meant herein that said composition is diluted by the user with an appropriate solvent, typically water. By "rinsing", it is meant herein contacting the surface, such as the dishware cleaned using a process according to the present invention with substantial quantities of appropriate solvent, typically water, after the step of applying the liquid composition herein onto said dishware. By "substantial quantities", it is meant usually about 1 to about 10 liters.

The composition herein can be applied in its diluted form. Soiled e.g. dishes are contacted with an effective amount, typically from about 0.5 ml to about 20 ml (per about 25 dishes being treated), preferably from about 3 ml to about 10 ml, of the detergent composition, preferably in liquid form, of the present invention diluted in water. The actual amount of detergent composition used will be based on the judgment of user, and will typically depend upon factors such as the particular product formulation of the composition, including the concentration of active ingredients in the composition, the number of soiled dishes to be cleaned, the degree of soiling on the dishes, and the like. Generally, from about 0.01 ml to about 150 ml, preferably from about 3 ml to about 40 ml of a liquid detergent composition of the invention is combined with from about 2000 ml to about 20000 ml, more typically from about 5000 ml to about 15000 ml of water in a sink having a volumetric capacity in the range of from about 1000 ml to about 20000 ml, more typically from about 5000 ml to about 15000 ml. The soiled dishes may be immersed in the sink containing the diluted compositions then obtained, where contacting the soiled surface of the dish with a cloth, sponge, or similar article cleans them. The cloth, sponge, or similar article may be immersed in the detergent composition and water mixture prior to being contacted with the dish surface, and is typically contacted with the dish surface for a period of time ranged from about 1 to about 10 seconds, although the actual time will vary with each application and user. The contacting of cloth, sponge, or similar article to the surface is preferably accompanied by a concurrent scrubbing of the surface.

Another method of the present invention will comprise immersing the soiled articles such as dishes into a water bath or held under running water without any detergent composition. A device for absorbing detergent composition, such as a sponge or pre-treat device, is placed directly into a separate quantity of undiluted detergent composition, preferably in the form of a liquid for a period of time typically ranging from about 1 to about 5 seconds. The absorbing device, and consequently the undiluted detergent composition, is then contacted individually to the surface of each of the soiled dishes to remove said soiling. The absorbing device is typically contacted with each surface for a period of time range from about 1 to about 10 seconds, although the actual time of application will be dependent upon factors such as the degree of soiling of the surface. The contacting of the absorbing device to the soiled surface is preferably accompanied by concurrent scrubbing.

Alternatively, the device may be immersed in a mixture of the detergent composition and water prior to being contacted with the soiled surface, the concentrated solution is made by diluting the detergent composition with water in a small container that can accommodate the cleaning device at weight ratios ranging from about 95:5 to about 5:95, preferably about 80:20 to about 20:80 and more preferably about 70:30 to about 30:70, respectively, of detergent composition, preferably in liquid form the ratio of detergent composition:water respectively depending upon the user habits and the cleaning task. These methods are particularly applicable to soiled articles which are dishware.

The detergent composition according to the invention might also be used as a laundry detergent composition, for use in or prior to the exposing the soiled items to an automatic, particularly semi-automatic washing machine. Following optional pretreatment, the soiled surface may be washed in a washing machine or otherwise rinsed. In machine methods soiled articles may be treated with an aqueous wash liquor in which an effective amount of a cleaning composition of the invention is dissolved or dispensed into therein. An "effective amount" of the cleaning composition is typically from about 10 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 30:1. The compositions may be employed at concentrations of from about 500 ppm to about 15,000 ppm in solution. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The present invention is particularly directed to manual washing methods or hand washing/soak methods, and combined manual washing with semi-automatic washing machines, are also included. Temperatures are typically lower, below 50, 45, 40, 35, 30, or 25° C.

EXAMPLES

Hereinafter, the present invention is described in more detail based on examples. All percentages are by weight unless otherwise specified.

Example 1

Exemplary Manual Dish-Washing Detergent Composition

| Level (as 100% active) | |
|---|---|
| Sodium alkyl ethoxy sulfate (C1213EO0.6S) | 22.91% |
| n-C12-14 Di Methyl Amine Oxide | 7.64% |
| Lutensol XP80 (non-ionic surfactant supplied by BASF) | 0.45% |
| Sodium Chloride | 1.2% |
| Poly Propylene Glycol | 1% |
| Ethanol | 2% |
| Sodium Hydroxide | 0.24% |
| Ole $T_{JE}$ (SEQ ID NO: 1) | 0.1 |
| Oleate hydratase | 0.02 |
| Minors (perfume, preservative, dye) + water | To 100% |
| pH (@ 10% solution) | 9 |

Example 2

Exemplary Liquid Laundry Detergent Compositions

The following liquid laundry detergent compositions are prepared by traditional means known to those of ordinary skill in the art by mixing the following ingredients.

| Ingredients (wt %) | 2A | 2B | 2C |
|---|---|---|---|
| AES[1] | 17 | 2 | 11 |
| LAS[2] | 2.8 | 15 | 10 |
| AE[3] | 2.3 | 2.37 | 3.44 |
| Citric Acid | 5 | 1.98 | — |
| Boric Acid | — | 1 | 3 |
| Amine Oxide | 1.2 | — | 0.5 |
| Trimethyl Lauryl Ammonium Chloride | — | 1.5 | — |
| PEI Polymer | 0.1~3.5 | 1 | 2 |
| Fatty Acids | 1.2 | 1.2 | 1.2 |
| Protease (54.5 mg/g)[4] | 7.62 | 7.98 | 2.08 |
| Amylase (29.26 mg/g)[5] | 2.54 | 2.67 | 0.69 |
| Xyloglucanase[6] | — | — | 0.15 |
| Ole $T_{JE}$ (SEQ ID NO: 1) | 0.01 | 0.1 | 0.1 |
| Borax | 4.72 | 4.94 | — |
| Calcium Formate | 0.15 | 0.16 | 0.16 |
| Amphiphilic polymer[7] | — | 1.5 | 4.36 |
| Hexamethylene diamine, ethoxylated, quaternized, sulfated[8] | — | — | 1.68 |
| DTPA[9] (50% active) | 0.28 | 0.3 | 0.64 |
| Tiron ® | 0.84 | 0.89 | — |
| Optical Brightener[10] | 0.34 | 0.37 | 0.36 |
| Ethanol | 0.97 | 4.1 | 2.99 |
| Propylene Glycol | 4.9 | 5.16 | 8.49 |
| Diethylene Glycol | — | — | 4.11 |
| Monoethanolamine (MEA) | 1.12 | 1.17 | 0.23 |
| Caustic Soda (NaOH) | 3.5 | 3.74 | 2.1 |
| Na Formate | 0.61 | 0.64 | 0.23 |
| Na Cumene Sulfonate | — | — | 1 |
| Suds Suppressor | — | — | 0.18 |
| Dye | 0.01 | — | 0.02 |
| Perfume | 0.85 | — | 1 |
| Preservative[11] | 0.05 | 0.5 | — |
| Hydrogenated castor oil | — | — | 0.27 |
| Water | Q.S. | Q.S. | Q.S. |

Example 3

Exemplary Liquid Detergent Compositions for Use in Unit Dose (UD) Products

The following liquid detergent compositions are prepared and encapsulated in a multi-compartment pouch formed by a polyvinyl alcohol-film.

TABLE 6

| | A | B |
|---|---|---|
| Usage (g) | 25.36 | 24.34 |
| Usage (ml) | 23.7 | 22.43 |
| Wash Volume (L) | 64 | 64 |
| Anionic/Nonionic ratio | 1.73 | 9.9 |
| Ingredients (wt %) | | |
| Linear $C_9$-$C_{15}$ Alkylbenzene sulfonic acid | 18.25 | 22.46 |
| HC24/25 AE2/3S 90/10 blend | 8.73 | 15.29 |
| $C_{12-14}$ alkyl 9-ethoxylate | 15.56 | 3.82 |
| Citric Acid | 0.65 | 1.55 |
| Fatty acid | 6.03 | 6.27 |
| Chelants | 1.16 | 0.62 |
| PEI Polymers | 1~6 | 3 |
| S Copolymers | 1~6 | 3 |
| Enzymes | 0.11 | 0.12 |
| Ole $T_{JE}$ (SEQ ID NO: 1) | 0.008 | 0.02 |
| Optical Brightener[15] | 0.18 | 0.19 |
| Structurant | 0.1 | 0.1 |
| Solvent system* | 20.31 | 17.96 |
| Water | 10.31 | 11.66 |
| Perfume | 1.63 | 1.7 |
| Aesthetics | 1.48 | 1.13 |
| Mono-ethanolamine or NaOH (or mixture thereof) | 6.69 | 9.75 |
| Other laundry adjuncts/minors | Q.S. | Q.S. |

*May include, but not limited to propanediol, glycerol, ethanol, dipropyleneglycol, polyetheyleneglycol, polypropyleneglycol.

Example 4

Granular Laundry Detergent Compositions for Hand Washing or Washing Machines, Typically Top-Loading Washing Machines

| Ingredient | 4A | 4B | 4C | 4D | 4E | 4F |
|---|---|---|---|---|---|---|
| | | | % weight | | | |
| LAS[2] | 11.33 | 10.81 | 7.04 | 4.20 | 3.92 | 2.29 |
| $C_{12-14}$ Dimethylhydroxyethyl ammonium chloride | 0.70 | 0.20 | 1.00 | 0.60 | — | — |
| AES[1] | 0.51 | 0.49 | 0.32 | — | 0.08 | 0.10 |
| AE[3] | 8.36 | 11.50 | 12.54 | 11.20 | 16.00 | 21.51 |
| Sodium Tripolyphosphate | 5.0 | — | 4.0 | 9.0 | 2.0 | — |
| Zeolite A | — | 1.0 | — | 1.0 | 4.0 | 1.0 |
| Sodium silicate 1.6 R | 7.0 | 5.0 | 2.0 | 3.0 | 3.0 | 5.0 |
| Sodium carbonate | 20.0 | 17.0 | 23.0 | 14.0 | 14.0 | 16.0 |
| Polyacrylate MW 4500 | 1.0 | 0.6 | 1.0 | 1.0 | 1.5 | 1.0 |
| Polymer grafted with vinyl acetate side chains[7] | 0.1 | 0.2 | — | — | 0.1 | — |
| Carboxymethyl cellulose | 1.0 | 0.3 | 1.0 | 1.0 | 1.0 | 1.0 |
| Acid Violet 50 | 0.05 | — | 0.02 | — | 0.04 | — |
| Violet DD thiophene azo dye (Milliken) | — | 0.03 | — | 0.03 | — | 0.03 |
| Protease[4] | 0.10 | 0.10 | 0.10 | 0.10 | — | 0.10 |
| Amylase[5] | 0.03 | — | 0.03 | 0.03 | 0.03 | 0.03 |
| Lipase (Lipex from Novozymes) | 0.03 | 0.07 | 0.30 | 0.10 | 0.07 | 0.40 |
| Cellulase (Celluclean from Novozymes) | 0.002 | — | 0.05 | — | 0.02 | — |
| Ole $T_{JE}$ (SEQ ID NO: 1) | 0.01 | 0.01 | 0.01 | 0.05 | 0.009 | 0.02 |
| Optical Brightener[15] | 0.300 | 0.011 | 0.370 | 0.850 | 0.10 | 0.710 |
| Chelant[13] | 0.60 | 0.80 | 0.60 | 0.25 | 0.60 | 0.60 |
| DTI[12] | 0.62 | 0.35 | 0.15 | 0.30 | 0.20 | 0.40 |
| Sodium Percarbonate | — | 5.2 | 0.1 | — | — | — |
| Sodium Perborate | 4.4 | — | 3.85 | 2.09 | 0.78 | 3.63 |
| Nonanoyloxy benzenesulphonate | 1.9 | 0.0 | 1.66 | 0.0 | 0.33 | 0.75 |
| Tetraacetylethylenediamine | 0.58 | 1.2 | 0.51 | 0.0 | 0.015 | 0.28 |
| Photobleach | 0.0030 | 0.0 | 0.0012 | 0.0030 | 0.0021 | — |
| S-ACMC[14] | 0.1 | 0.0 | 0.0 | 0.0 | 0.06 | 0.0 |
| Sulfate/Moisture | | | Balance | | | |

[1]AES can be $AE_{1.5}S$, $AE_2S$, and/or $AE_3S$, in the amount ranging from 0-20%.
[2]LAS can be provided in the amount ranging from 0-20%. [3]AE is a C12-14 alcohol ethoxylate, with an average degree of ethoxylation of 7-9, supplied by Huntsman, Salt Lake City, Utah, USA. It can be provided in the amount ranging from 0-10%.
[4]Proteases may be supplied by Genencor International, Palo Alto, California, USA (e.g., Purafect Prime ®, Excellase ®) or by Novozymes, Bagsvaerd, Denmark (e.g. Liquanase ®, Coronase ®).
[5]Available from Novozymes, Bagsvaerd, Denmark (e.g., Natalase ®, Mannaway ®). [6]Available from Novozymes (e.g., Whitezyme ®).
[7]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units, available from BASF as Sokalan PG101 ®.
[8]A compound having the following general structure: $bis((C_2H_5O)(C_2H_4O)_n)(CH_3)—N^+—C_xH_{2x}—N^+—(CH_3)\text{-}bis((C_2H_5O)(C_2H_4O)_n)$, wherein $n$ = from 20 to 30, and $x$ = from 3 to 8, or sulphated or sulphonated variants thereof, available from BASF as Lutenzit Z96 ®
[9]DTPA is diethylenetriaminepentaacetic acid supplied by Dow Chemical, Midland, Michigan, USA. [10]Suitable Fluorescent Whitening Agents are for example, Tinopal ® AMS, Tinopal ® CBS-X, Sulphonated zinc phthalocyanine Ciba Specialty Chemicals, Basel, Switzerland. It can be provided in the amount ranging from 0-5%.
[11]Suitable preservatives include methylisothiazolinone (MIT) or benzisothiazolinone (BIT), which can be provided in the amount ranging from 0-1%. [12]DTI is poly(4-vinylpyridine-1-oxide) (such as Chromabond S-403E ®) and/or poly(1-vinylpyrrolidone-co-1-vinylimidazole) (such as Sokalan HP56 ®). [13]Chelant is diethylene triamine pentaacetic acid, 1-hydroxyethane 1,1-diphosphonic acid and/or sodium salt of ethylenediamine-N,N'-disuccinic acid, (S,S) isomer (EDDS)
[14]S-ACMC is Rective Blue 19 Azo-CM-Cellulose provided by Megazyme [15]Optical brightener is disodium 4,4'-bis{[4-anilino-6-morpholino-s-triazin-2-yl]-amino}-2,2'-stilbenedisulfonate, disodium 4,4'-bis-(2-sulfostyryl)biphenyl (sodium salt) and/or Optiblanc SPL10 ® from 3V Sigma All percentages and ratios given for enzymes are based on active protein. All percentages and ratios herein are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A detergent composition comprising a fatty acid decarboxylase enzyme having at least 95% sequence identity to the amino acid sequence of SEQ ID NO: 1 and a surfactant system, wherein the fatty acid decarboxylase enzyme is defined by an enzyme/cofactor/co-substrate system capable of catalyzing the conversion of any C10-20 saturated, mono-unsaturated or polyunsaturated fatty acid into its corresponding terminal alkene as shown in reaction Scheme 1 and wherein the co-substrate is $H_2O_2$:

Scheme 1

2. A detergent composition according to claim 1 wherein the fatty acid decarboxylase enzyme is selected from the group consisting of cytochrome P450 and mixtures thereof.

3. A detergent composition according to claim 1 wherein the fatty acid decarboxylase enzyme is selected from the group of families consisting of $CYP_{BS\beta}$ and $CYP_{SP\alpha}$.

4. A detergent composition according to claim 1 additionally comprising a source of hydrogen peroxide.

5. A detergent composition according to claim 1 comprising one or more additional enzymes.

6. A detergent composition according to claim 5 comprising one or more additional enzymes selected from the group consisting of protease, amylase, lipase, cellulase, lipoxgenase, carbohydrate oxidase and oleate hydratase, and mixtures thereof.

7. A detergent composition according to any claim 6 wherein the additional enzyme is selected from lipase, lipoxgenase, carbohydrate oxidase, oleate hydratase and mixtures thereof.

8. A detergent composition according to claim 1 wherein the fatty acid decarboxylase enzyme is present in an amount from 0.0001 wt % to 1 wt % based on active protein.

9. A detergent composition according to claim 1 wherein the surfactant system comprises one or a mixture of more than one surfactant and is present in an amount from 5 to 80 wt % of the composition.

10. A detergent composition according to claim 9 wherein the surfactant system comprises a non-ionic surfactant.

11. A composition according to claim 1 wherein the surfactant system comprises an amphoteric and/or a zwitterionic surfactant in addition to the anionic surfactant.

12. A composition according to claim 11 wherein the anionic surfactant and the amphoteric and/or the zwitterionic surfactant are in a weight ratio of from about 5:1 to about 1:1.

13. A composition according to claim 11 wherein the amphoteric surfactant comprises an amine oxide surfactant and the zwitterionic surfactant comprises a betaine surfactant.

14. A detergent composition according to claim 1 wherein the composition is a manual dish-washing composition.

15. A composition according to claim 1 additionally comprising an enzyme stabilizer.

16. A composition according to claim 1 additionally comprising a chelant selected from the group consisting of amino carboxylates or amino phosphonates and mixtures thereof.

17. A method of manually washing soiled articles, comprising the step of: delivering a composition according to claim 1 to a volume of water to form a wash liquor and immersing the soiled articles, in the wash liquor.

18. A method of manually washing soiled articles, comprising the step of: delivering a composition according to claim 1 directly onto a soiled article, or onto a cleaning implement and using the cleaning implement to clean the soiled article.

19. A detergent composition according to claim 10 wherein the surfactant system comprises both anionic and non-ionic surfactant.

* * * * *